(12) United States Patent
Aoshima et al.

(10) Patent No.: US 7,372,553 B2
(45) Date of Patent: May 13, 2008

(54) APPARATUS AND METHOD FOR DETECTING DEFECT IN OPTICAL FIBER, AND PLASTIC OPTICAL FIBER MANUFACTURING APPARATUS

(75) Inventors: Shinsuke Aoshima, Shizuoka (JP); Shinji Higaki, Shizuoka (JP); Yoshiaki Shibano, Shizuoka (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 10/594,682

(22) PCT Filed: Mar. 29, 2005

(86) PCT No.: PCT/JP2005/006573

§ 371 (c)(1),
(2), (4) Date: Sep. 28, 2006

(87) PCT Pub. No.: WO2005/095930

PCT Pub. Date: Oct. 13, 2005

(65) Prior Publication Data

US 2007/0188739 A1    Aug. 16, 2007

(30) Foreign Application Priority Data

Mar. 30, 2004    (JP) .......................... 2004-100657

(51) Int. Cl.
*G01N 21/00*    (2006.01)

(52) U.S. Cl. .................................................... 356/73.1
(58) Field of Classification Search ................ None
See application file for complete search history.

(56) References Cited

U.S. PATENT DOCUMENTS 5,185,636 A * 2/1993 Button et al. ............... 356/73.1
7,038,191 B2 * 5/2006 Kare et al. ............. 250/227.11

FOREIGN PATENT DOCUMENTS

| JP | 61-130904 A | 6/1986 |
|---|---|---|
| JP | 6-331557 A | 12/1994 |
| JP | 8-208264 A | 8/1996 |
| JP | 10-68700 A | 3/1998 |
| JP | 11-271175 A | 10/1999 |
| JP | 2000-281379 A | 10/2000 |
| JP | 2000-351646 A | 12/2000 |
| JP | 2001-235396 A | 8/2001 |
| JP | 3332922 B2 | 7/2002 |

* cited by examiner

*Primary Examiner*—Tu T Nguyen
(74) *Attorney, Agent, or Firm*—Sughrue Mion, PLLC

(57) ABSTRACT

While a plastic optical fiber (POF) strand is guided by guide pulleys toward a winding machine, an internal defect in the POF strand is detected by a defect detection apparatus. The defect detection apparatus includes at least one light illumination device, at least one imaging device and at least one defect detection unit. The light illumination device illuminates the POF strand, and the imaging device takes an image of the POF strand and outputs signal to the detection unit.

13 Claims, 7 Drawing Sheets

APPARATUS AND METHOD FOR DETECTING DEFECT IN OPTICAL FIBER, AND PLASTIC OPTICAL FIBER MANUFACTURING APPARATUS

CROSS REFERENCE TO RELATED APPLICATIONS

This application is National Stage Entry of PCT/JP05/06573 filed Mar. 29, 2005. Further, this application claims the benefit of Japanese Patent Application No. 2004-100657 filed on Mar. 30, 2004, in the Japanese Patent Office.

TECHNICAL FIELD

The present invention relates to an apparatus and a method for detecting a defect in an optical fiber, and a plastic optical fiber manufacturing apparatus that can detect a defect in the optical fiber in manufacture.

BACKGROUND ART

A plastic optical part has merits of design facility and low manufacture cost, compared with a glass optical part with identical structure, so the plastic optical part has been recently utilized as an optical fiber, an optical lens element, an optical waveguide and so forth. Especially, a plastic optical fiber (referred to as "POF"), entirely composed of a plastic is suitable for manufacture of the optical fiber with large diameter at a low cost, because the POF has advantages in excellent flexibility, light weight and high machinability, compared with the glass optical fiber. Accordingly, it is planned to utilize the plastic optical fiber as an optical transmission medium for short-distance purpose in which the transmission loss is small.

The POF is composed of a core part, having organic compounds as the main component, in which a polymer forms a matrix, and a cladding part composed of organic materials having different refractivity from the core part. A graded index (GI) type POF, in which the refractive index in the core part gradually decreases from the center to the surface of the core part, has high transmission band and high transmission capacity. Various methods for manufacture of the GI type POF are disclosed (for example, Japanese Laid-Open Patent Publication (JP-A) No. 2002-220261 and U.S. Pat. No. 5,541,247 (counterpart of Japan Patent No. 3332922)). For example, the GI type POF is manufactured by forming an optical fiber base body (hereinafter referred to as "preform") by use of surface gel polymerization, and then by melt-drawing the preform.

When the preform contains microscopic bubbles during the manufacture process, such bubble becomes a cavity as an internal defect that extends in the lengthwise direction of the optical fiber strand after the melt-drawing process. Such cavities would cause decrease in transmission property and physical strength of the optical fiber.

In manufacture of the glass optical fiber, JP-A 2000-281379 discloses a defect detection apparatus provided with the extension machine so that the bubbles (internal detect) in the optical fiber is detected during the manufacture. This defect detection apparatus has a light emission member and a light detection member to detect the bubbles in the optical fiber. When the detection light from the light emission member is scattered by the bubble in the optical fiber, the light amount detected by the light detection member is decreased. Thereby, it is possible to detect the bubbles in the optical fiber. Also, in JP-A 2001-235396, laser beam from the light emitting member is scattered by the bubbles in the optical fiber, and the intensity of the scattered light is detected by an image sensor as the light detecting member. Based on the intensity distribution of the forward scatter, it is possible to detect the bubbles in the optical fiber.

In the method to detect a defect by use of forward scatter, as described in JP-A 2000-281379 and JP-A 2001-235396, the detection accuracy becomes worse since the diameter of the fiber strand of the POF is relatively large, compared with the glass optical fiber. For example, because of decrease in detection accuracy, the conventional defect detection apparatus can not detect microscopic bubbles having the diameter of 10-30 μm. Moreover, the method to detect defect by use of forward scatter will generate undetectable region in the fiber strand having large diameter.

An object of the present invention is to provide an apparatus and a method for detecting an internal defect in a plastic optical fiber with high precision.

Another object of the present invention is to provide a plastic optical fiber manufacturing apparatus that can detect the defect in manufacture.

DISCLOSURE OF INVENTION

The above objects are achieved by illuminating detection light to the optical fiber from a direction that crosses the axis of the optical fiber; taking an image of the optical fiber illuminated by the detecting light from a direction that crosses the optical axis of the detection light and outputting light intensity distribution signals over the radial direction perpendicular to the axis of the optical fiber; obtaining the light intensity distribution signals continuously in the axial direction of the optical fiber; and detecting the internal defect based on the level of the light intensity distribution signals in the radial direction and the axial direction.

The apparatus for detecting an internal defect in the optical fiber comprises a detection light illumination device, an imaging device and a defect detection section. The detection light illumination device illuminates detection light to the optical fiber from a direction that crosses the axis of the optical fiber. The imaging device takes an image of the optical fiber illuminated by the detection light from a direction that crosses the optical axis of the detection light, and outputs light intensity distribution signals in the radial direction perpendicular to the axis of the optical fiber. The defect detection section obtains the light intensity distribution signals continuously along the axial direction of the optical fiber, and detects the internal defect based on the level of the light intensity distribution signals in the radial direction and the axial direction.

In a preferred embodiment, more than two pairs of the detection light illumination device and the imaging device are arranged along the axial direction of the optical fiber, and the imaging devices are arranged at a regular interval around the optical fiber. The imaging device is a line sensor camera having plural imaging elements in line, and the detection light illumination device is located such that the light axis of the illumination light is in the opposite side of the line sensor camera with respect to the axis of the optical fiber.

The defect detection section sets a detection start position in which the level of the light intensity distribution signal in the radial direction becomes more than a scan start threshold value, and sets a defect detection range based on the detection start pixel and the type of the optical fiber. The detection start position is set when the line sensor camera repeats to take the image of the optical fiber by a predetermined time.

Then, the existence of the internal defect is determined based on the size of the portion in the defect detection range in which the level of the light intensity distribution signal is more than a defect judgment value. The light intensity distribution signals in the radial and the axial direction are converted into binary data based on the defect judgment threshold value. Then, a blob process is carried out to combine the pixels corresponding to the position in which the light intensity signal is more than the second threshold value, and the existence of the internal defect is determined when the size of the combined area is a first standard size or more.

The internal defect is judged as a microscopic bubble when the size of the combined area is a first standard size or more and a second standard size or less. And the internal defect is judged as a bubble in a drawing process when the size of the combined area is the second standard size.

A marking device may be provided with the apparatus in order to put a marking on the optical fiber at a position of the defect. The diameter of the optical fiber to be examined is 250 µm or more. The optical fiber is a plastic optical fiber strand formed by melt-drawing a preform.

A optical fiber manufacturing apparatus is preferably have the defect detection apparatus described above so that the internal defect in the optical fiber is detected during the manufacture of the optical fiber.

According to the present invention, it is possible to increase the precision of defect detection, compared with the method to detect the defect by use of forward scatter. Moreover, since more than two pairs of the imaging device around the optical fiber can cover the whole area of the optical fiber to be examined, it is possible to prevent undetectable region in the fiber strand having large diameter.

BEST MODE FOR CARRYING OUT THE INVENTION

Figure 1:
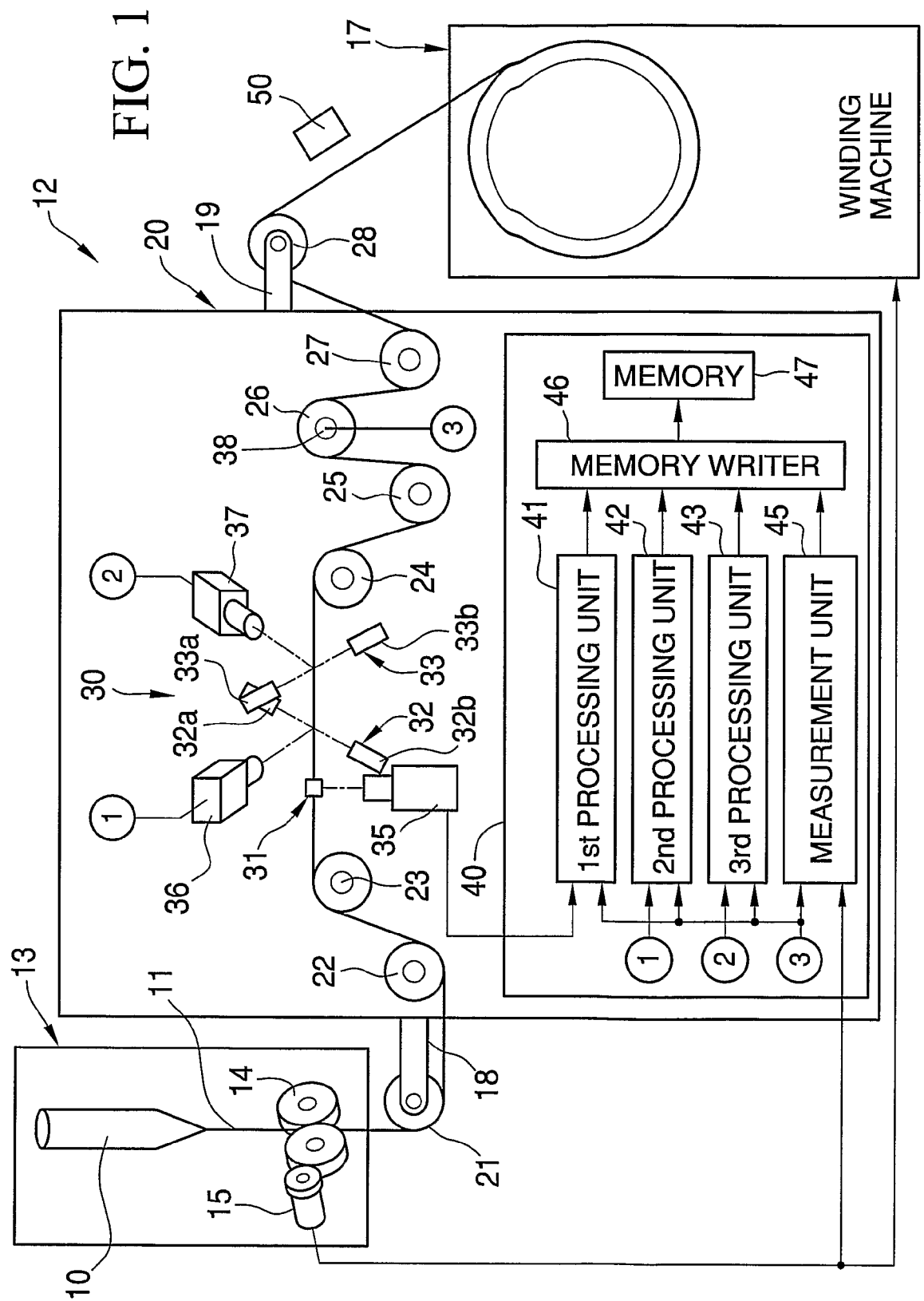
FIG. 1 is a schematic illustration of a manufacture line in which a plastic optical fiber (POF) strand is drawn from a preform and wound in a winding machine.
Figure 2A:
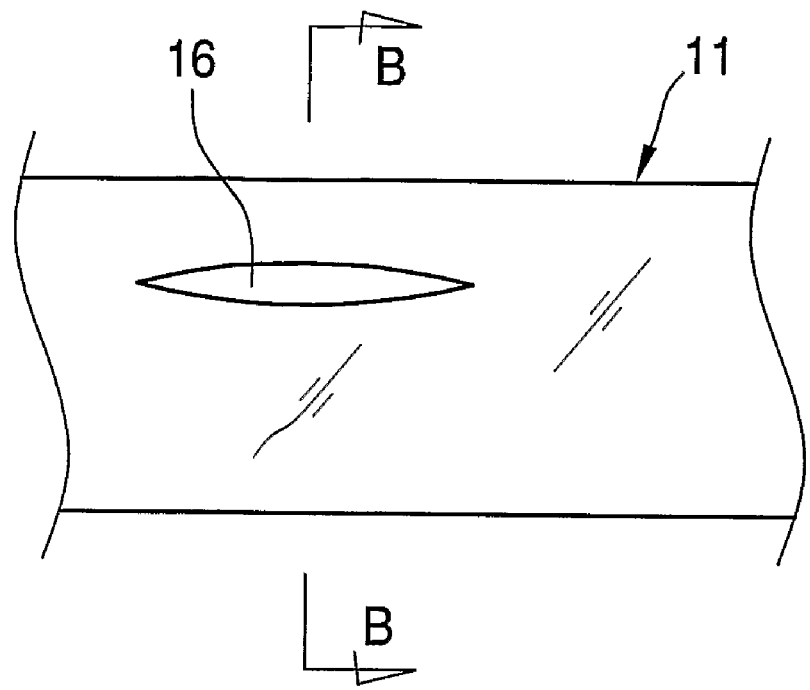
FIG. 2A is a side view of a bubble (defect) in the POF strand.
Figure 2B:
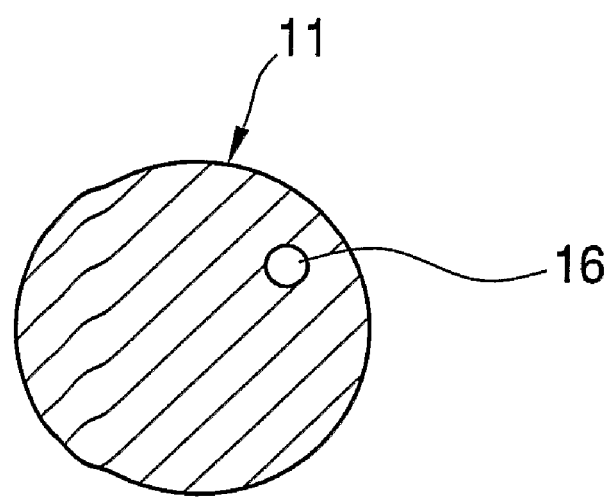
FIG. 2B is a cross section taken on the line B-B of FIG. 2A.

In FIG. 1, a manufacture line 12 for winding a POF strand 11 that is drawn from a preform 10. In a well-known drawing machine 13, a preform 10 is heated, and the molten preform 10 is drawn by a drawing roller pair 14. The POF strand after the drawing process is fed to a defect detection apparatus 20 according to the present invention in which a defect 16 (see FIG. 2A) in the POF strand 11 is detected. For instance, the defect 16 in the POF strand 11 is a bubble. After the POF strand 11 passes the defect detection apparatus 20, the POF strand 11 is wound around a roll in a winding machine 17.

In the drawing machine 13, an encoder 15 connected to the drawing roller pair 14 outputs measurement signals that indicate the feeding length of the POF strand 11 by the drawing roller pair 14. The measurement signals are sent to the defect detection apparatus 20 and the winding machine 17 for the purpose of correcting the feeding length in the defect detection apparatus 20 and the winding machine 17.

The defect detection apparatus 20 comprises first to eighth guide pulleys 21-28 that guide the POF strand 11 toward the defect detection unit 30. The first guide pulley 21 and the eighth guide pulley 28 are supported by support arms 18, 19, respectively. The first guide pulley 21 guides the POF strand 11 from the drawing machine 13 to the defect detection apparatus 20. The eighth guide pulley 28 guides the POF strand 11 from the defect detection apparatus 20 to the winding machine 17.

Figure 3A:
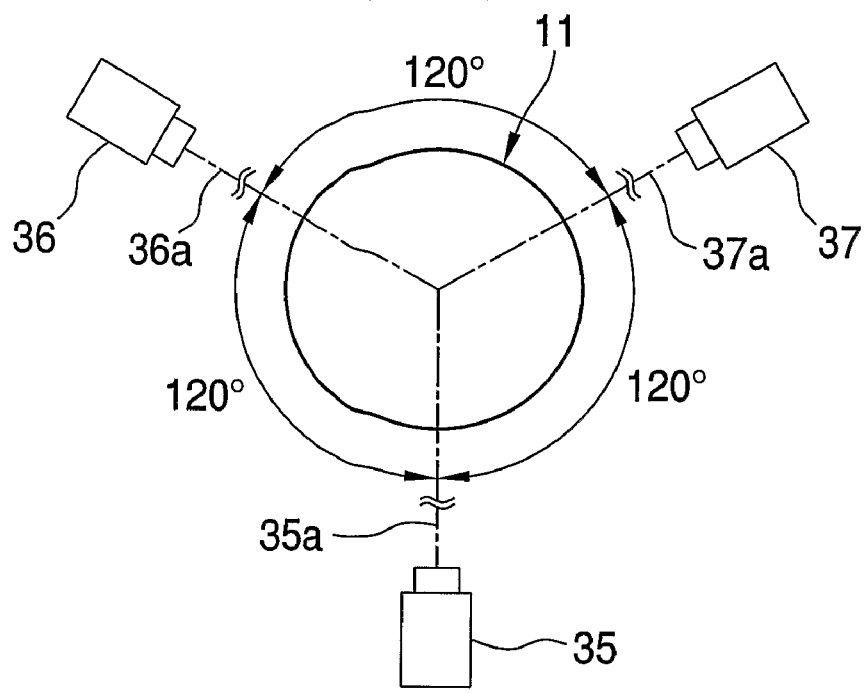
FIG. 3A is an explanatory view of an arrangement of line sensor cameras.

The defect detection unit 30 is provided between the third guide pulley 23 and the fourth guide pulley 24. The defect detection unit 30 has first to third light emission devices 31-33, and first to third line sensor cameras 35-37 that are arranged at regular pitches in the feeding direction of the POF strand 11. The light emission devices 31-33 are the same, and arranged at 120 degree interval around the POF strand 11 (120 degree rotational symmetry around the POF strand 11). The line sensor cameras 35-37 are the same, and arranged at 120 degree interval around the POF strand 11 (see FIG. 3A).

Figure 3B:
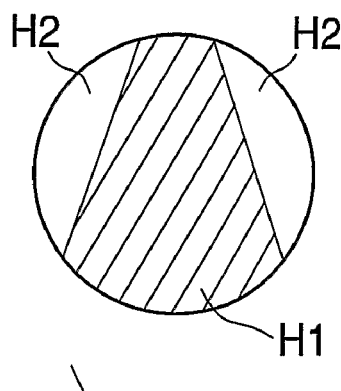
FIGS. 3B, 3C, 3D and 3E are explanatory views of scanned areas of the line sensor cameras.
Figure 3C:
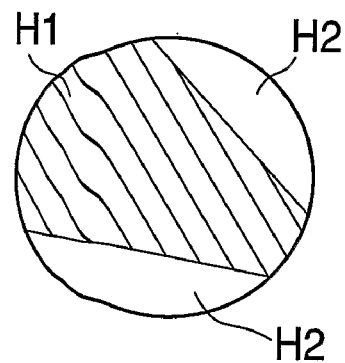
Figure 3D:
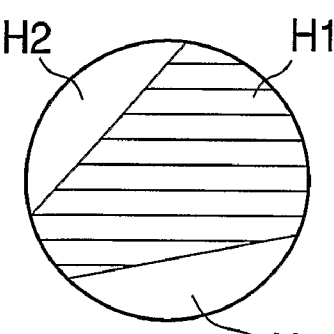

The reason of such arrangement of the light emission devices 31-33 and the line sensor cameras 35-37 is as follows. When a lateral side of a transparent pillar (such as POF strand 11) is taken by a camera, the camera can take the image of only a hatched area H1 in the cross section of the transparent pillar because of refraction at the air/resin interface. As shown in FIGS. 3B, 3C and 3D, the hatched area H1 extends about 105° in the camera side and about 35° in the opposite side, and thus each of the line sensor cameras 35-37 can not take an image of a non-hatched area H2 in the cross section of the POF strand 11.

Figure 3E:
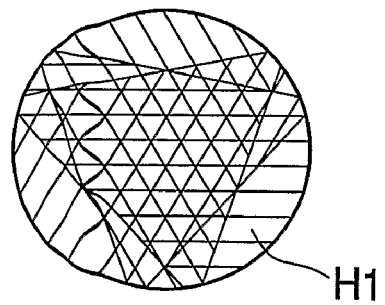

In this preferred embodiment, the line sensor cameras 35-37 are arranged to form 120 degree rotational symmetry around the POF strand 11, the first, second and third line sensor cameras 35-37 can capture the hatched area H1 shown in FIGS. 3B, 3C and 3D, respectively. Thus, by combining these hatched areas H1 of FIGS. 3B, 3C and 3D, it is possible to scan the whole cross section of the POF strand 11, as shown in FIG. 3E.

In order to examine the whole area of the cross section of the POF strand 11, it is necessary to scan the POF strand 11 from at least three directions, but it is possible to increase the directions to scan the POF strand 11. Scanning the POF strand 11 from three or four directions is preferable, and more preferably from three directions. It is not preferable to increase the number of the examination unit (light emission device and the line sensor camera), because of the following reasons. One reason is that the defect detection apparatus 20 becomes too large because it is necessary to arrange the examination units at certain intervals along the feeding path of the POF strand 11 for the purpose of preventing the illumination light from one examination unit from disturbing the operation of other examination unit. Another reason is that, because the scanned areas of the examination units are overlapped, synchronizing the operation of the examination units becomes too complicated.

Figure 4:
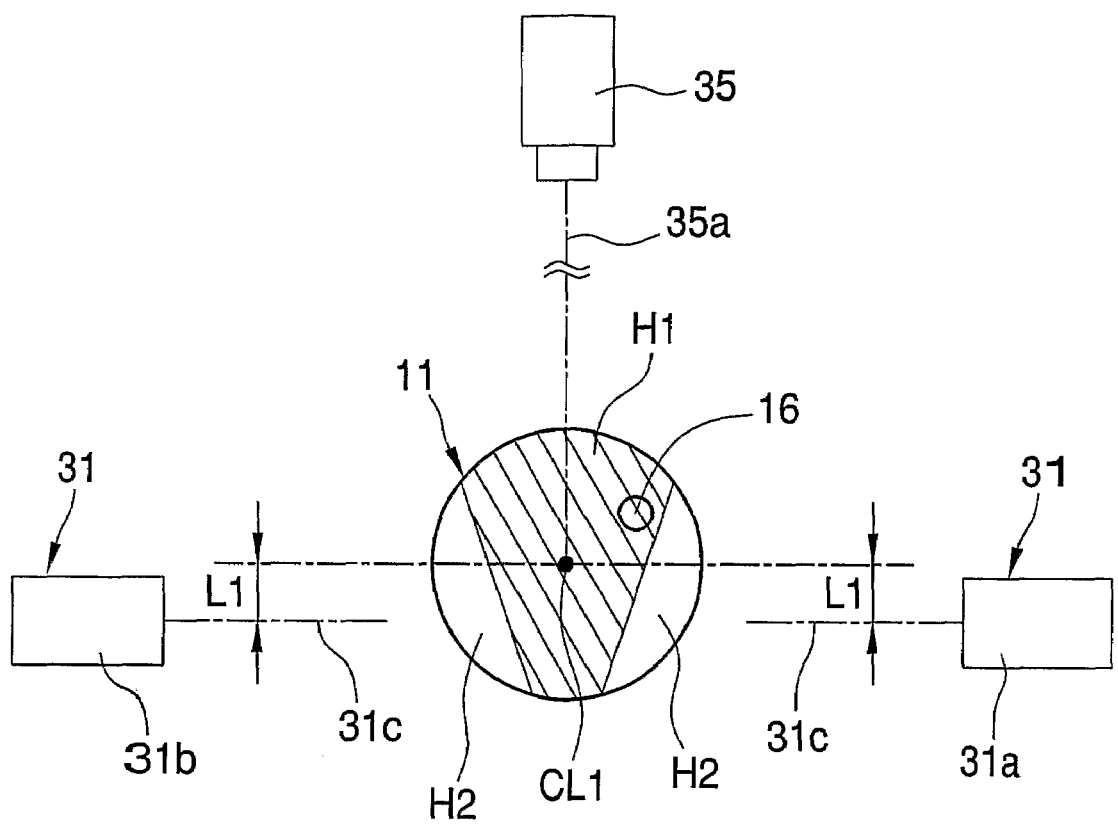
FIG. 4 is an explanatory view of an arrangement of a line sensor camera, light emission devices and the POF strand.

In FIG. 4, an example of the arrangement of the first light emission device 31 and the first line sensor camera 35 is illustrated. The second and third light emission devices 32, 33, and the second and third line sensor cameras 36, 37 are arranged in the same manner, so only the features of the first light emission device 31 and the first line sensor camera 35 are explained in this embodiment. The optical axis 35a of the line sensor camera 35 passes the center line CL1 of the POF strand 11 and takes the image of the POF strand 11 to obtain the intensity distribution in the radial direction of the POF strand 11. The line sensor camera 35, manufactured by DALSA Co., Ltd., for example, has about 96 imaging elements arranged in line. The image signals obtained by the line sensor camera 35 is digitally converted by an A/D converter circuit, and then sent to the first processing unit 41 in the controller 40 (see FIG. 1) as image data of the line image. The controller 40 for controlling the operation of the defect detection apparatus 20 comprises first to third processing units 41-43, a measurement unit 45, a memory writer 46 and a memory 47.

In FIG. 4, the first light emission device 31 comprises a pair of light emitting diodes 31a, 31b. The POF strand 11 is located between the light emitting diodes 31a, 31b. The POF strand 11 is illuminated by the light emitting diodes 31a, 31b from both sides. The number of the light emitting diodes is not limited to two, but it is possible to provide one light emitting diode or more than two light emitting diodes. Instead of the light emitting diodes, alternative light source such as a laser and a halogen lamp may be provided. In addition, the light emission device 31 may have a light emitting element (a light emitting diode, for example) and a light detecting element (a photo transistor, for example). In that case, a driver controls the light amount of the light emitting element based on the signals from the light detecting element.

The illumination light axis 31c of the first light emitting device 31 is shifted to the side opposite to the line sensor camera 35 by the length L1 from the center line CL1 of the POF strand 11. The amount of the length L1 can be changed in accordance with the diameter of the illumination light beam and the light amount of the first light emission device 31. In this embodiment in which the diameter of the POF strand is 316 μm and the diameter of the illumination beam is 5 mm, the shifted length L1 is 2.5-3.0 μm. By positioning the light emitting diodes in the side opposite to the line sensor camera 35, the illumination light from the light emitting diodes 31a, 31bis not reflected toward the line sensor camera 35, and thereby it is possible to prevent an incorrect action of the defeat detection apparatus 20. The direction of the illumination light may not be perpendicular to the imaging light axis of the line sensor camera 35. The direction of the illumination light may be inclined by about ±10° to the imaging light axis, although the inclination depends on the diffusion of the illumination light. The diameter of the POF strand 11 is preferably 250 μm or more.

Referring to FIG. 1, an encoder 38 is provided with the sixth guide pulley 26. The encoder 38 outputs measurement signals, which indicates the feeding length of the POF strand 11, to the measurement unit 45 of the controller 40. The measurement unit 45 calculates the length data (measurement data) that indicates the length from the sixth pulley 26 to the leading end of the POF strand 11. In calculating the length data, the measurement unit 45 refers the signals from the encoder 15 in the drawing machine 13 for correcting the length data. The calculated length data is correlated with the defect signals from the first to third processing units 41-43, which will be explained later, to specify the position of the defect in the POF strand 11. The encoder 38 generates the measurement signals each time the POF strand 11 is fed by 5 μm, for example.

Each of the image processing units 41-43 inputs the image data from the corresponding line sensor cameras 35-37 at a regular timing on the basis of the measurement signals from the encoder 38, so the image processing units 41-43 obtain successive image data in relation with the feeding length of the POF strand 11, thereby image data of the POF strand 11 in the axial and the radial directions can be obtained. In order to detect scattered light (white image) that indicates the defect 16, the first processing unit 41 carries out image processing to the image data from the line sensor camera for each 100 lines.

Figure 5:
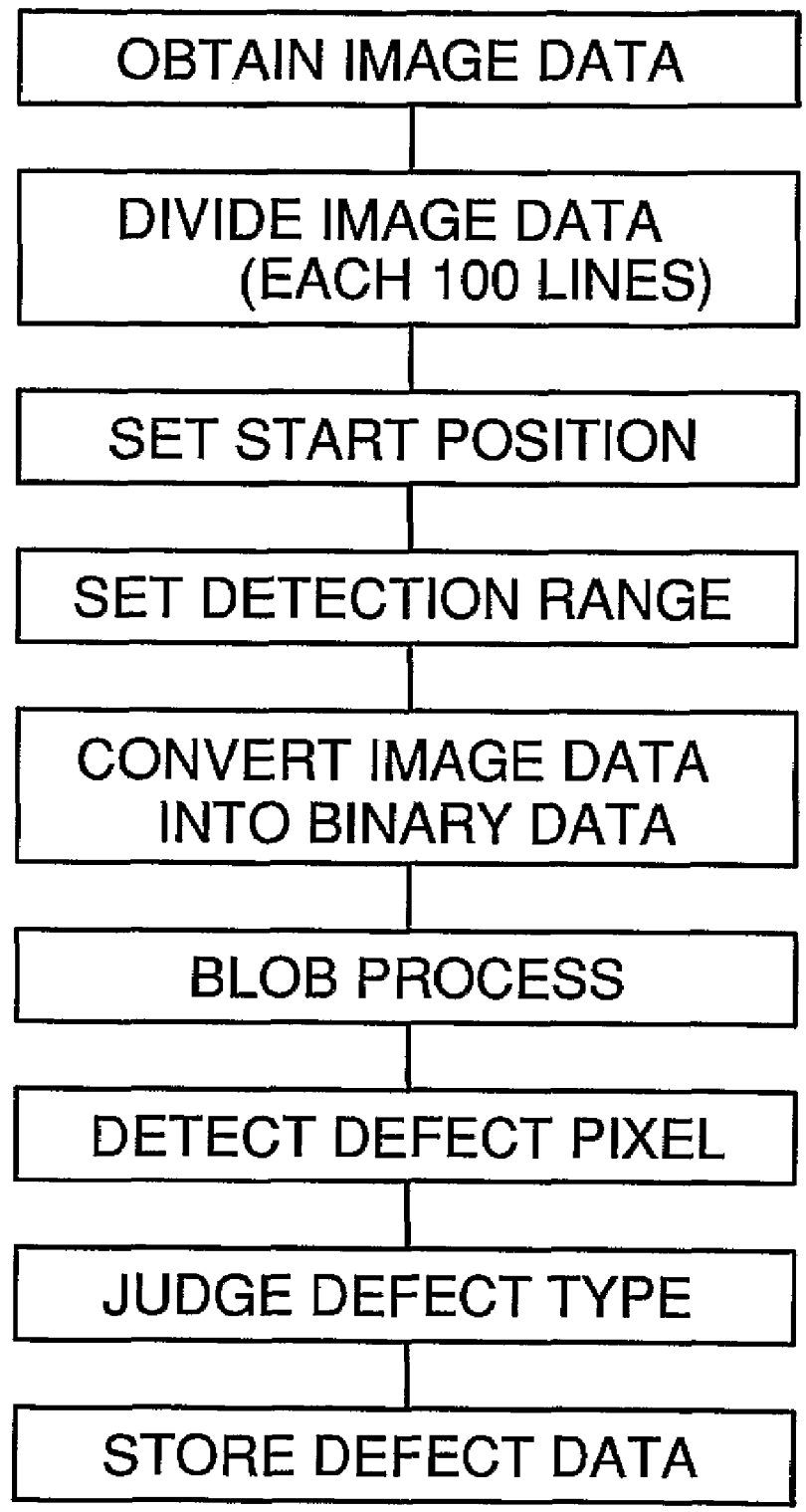
FIG. 5 is a flow chart of a defect detection process that is carried out by a processing unit.
Figure 6:
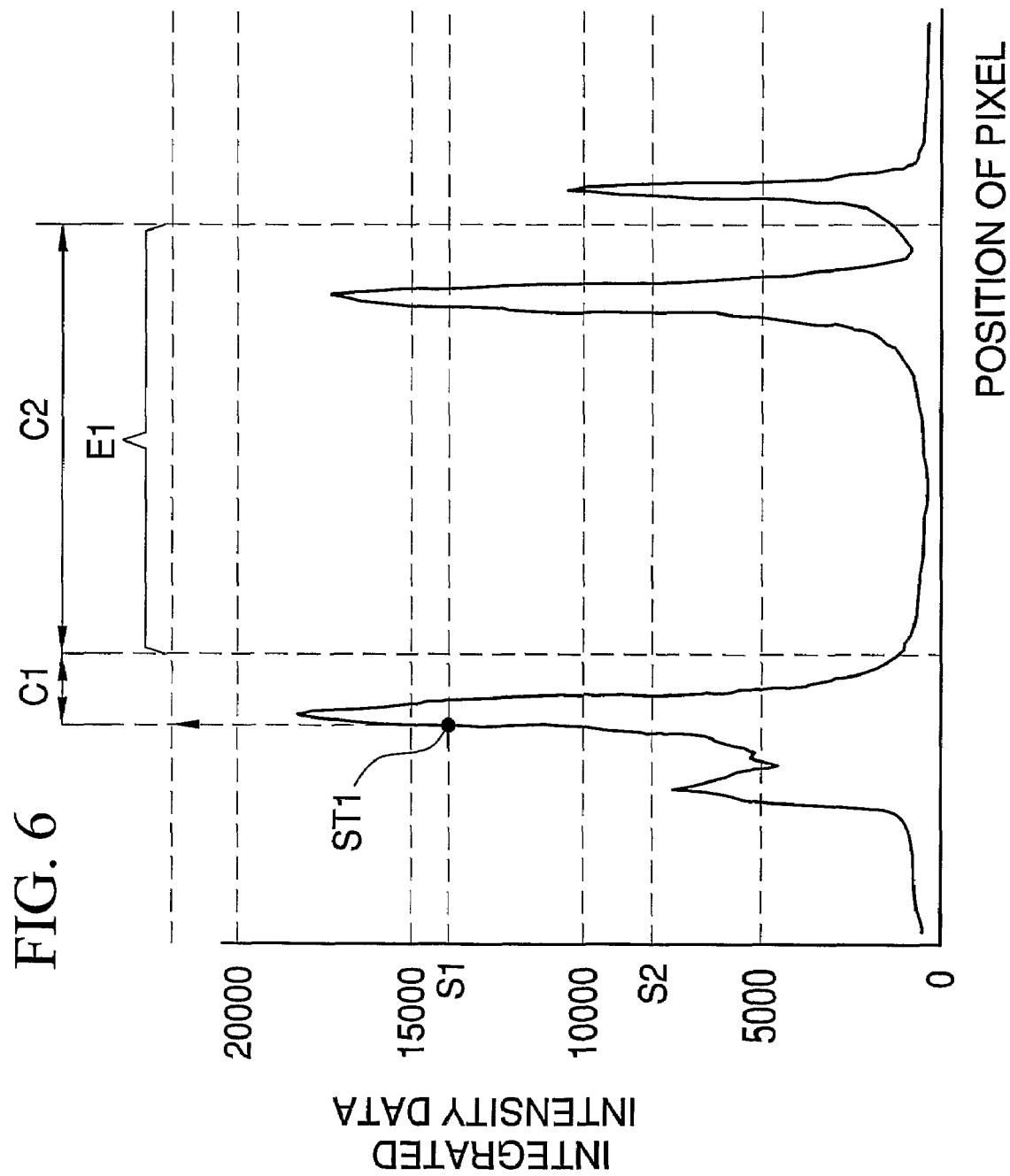
FIG. 6 is a graph showing intensity data in relation to the pixel position of the line sensor camera, in which a defect threshold level and a scan start threshold level are indicated.

FIG. 5 shows an example of the image processing sequences by the first processing unit 41. The graph in FIG. 6 shows an example of image data of one line obtained by the line sensor camera 35. In FIG. 6, the horizontal axis indicates the pixel position of the line sensor camera 35, and the vertical axis indicates a value of integrated intensity data. After the image data is obtained, the first processing unit 41 divides the obtained image data into image data of 100 lines. Then, the first processing unit 41 retrieves the image data for the first line in the 100 lines, and compares the intensity data in each pixel of the linear image data with a scan start threshold value S1 from the leftmost pixel to the rightmost pixel in this embodiment (in the radial direction of the POF strand 11). When the value of the intensity data becomes more than the scan start threshold value S1, the first processing unit 41 sets such pixel as the start position ST1. Since such pixel takes the image of the light source, it is possible to specify the start position ST1 on the basis of the surface that is continuously illuminated by the light source in the captured image.

Next, from the start position ST1, the first processing unit 41 specifies a detection range E1 based on a detection start position value C1 and a detection range value C2, which are predetermined in accordance with the size of the POF strand 11. Thus, when the start position ST1 is set, the detection range E1 is automatically set as well.

Within the detection range E1, the first processing unit 41 converts the intensity data for 100 lines into binary image data by use of a defect threshold Level S2. In other words, when the value of the intensity data of a pixel is more than the defect threshold value S2, such pixel is defined as the white pixel WP (see FIG. 7A). On the other hand, when the value of the intensity data is equal or less than the defect threshold value S2, such pixel is defined as the black pixel BP. The first processing unit 41 sets the start position ST1, the detection range E1 and the white pixels WP for each 100 lines. Then, the binary image data of adjoining 100 lines is connected to each other, so that the binary image data in the detection range E1 is obtained. Even if the POF strand 11 is undulated, it is possible to correct the effect of undulation because the binary image data is obtained from the image data of certain length (100 lines in this embodiment).

Figure 7A:
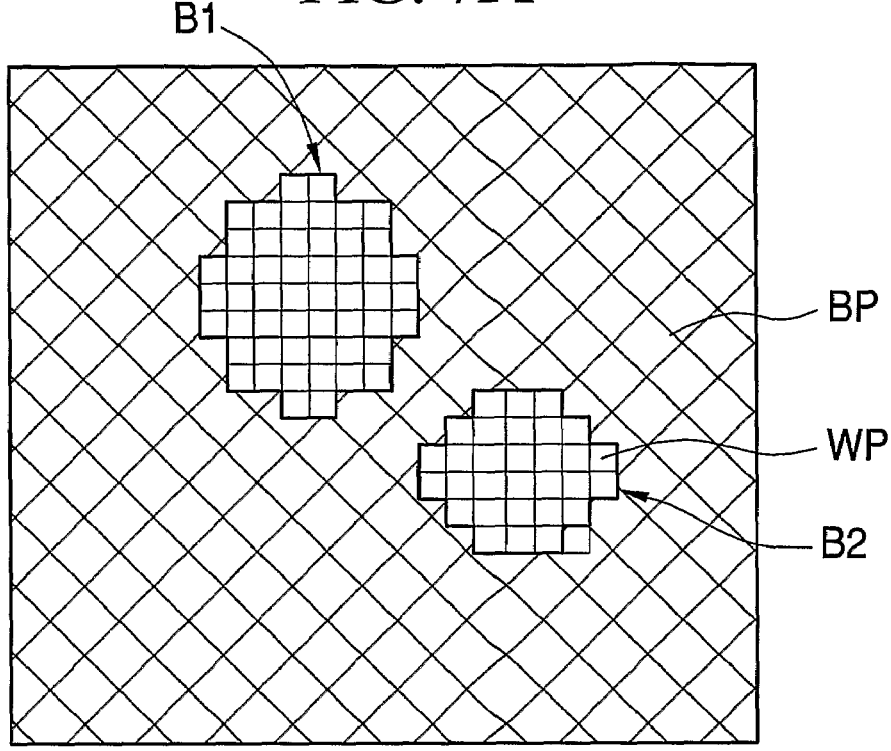
FIGS. 7A and 7B are explanatory views of detected blobs after blob generation process.
Figure 7B:
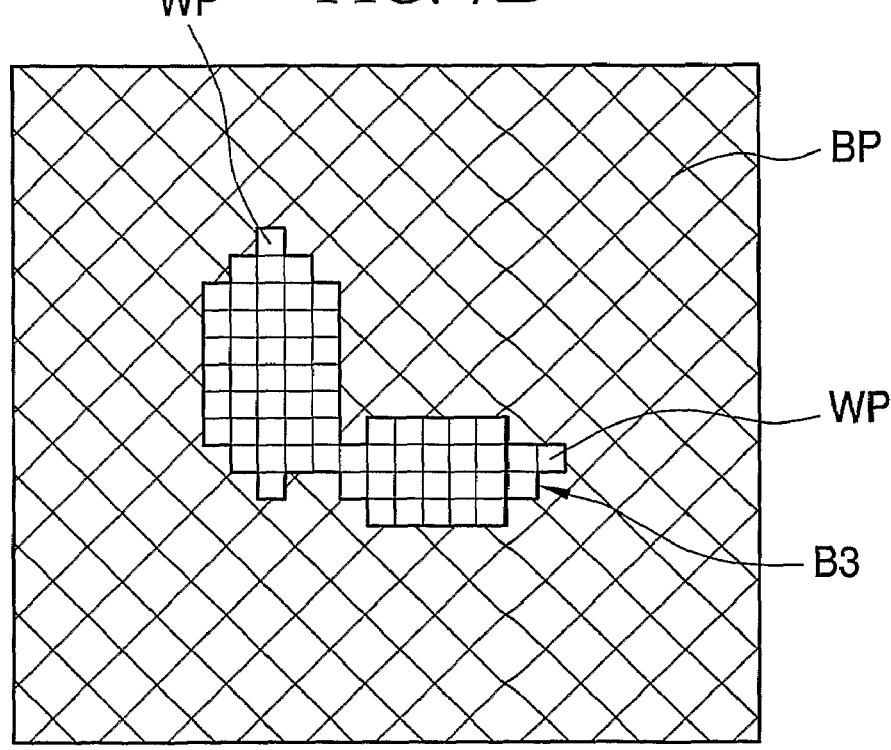

After the binary image data is obtained, so-called blob process is carried out. In the blob process, the first processing unit 41 determines if the white pixels WP are connected to each other in at least one of the four direction (left, right, up and down), and combines the adjoining white pixels WP. FIGS. 7A and 7B show examples of the result of the blob process. In FIG. 7A, two blobs B1, B2 are detected. In FIG. 7B, a single blob B3 is detected.

Besides the information of the scan start threshold level S1, the detection start position value C1, the detection range value C2, an internal memory of the first processing unit 41 stores information of a minimum blob value and defect type judgment value in accordance with the diameter of the POF strand 11. The minimum blob value indicates the minimum size (pixels) of the defect to be determined. The defect type judgment value is utilized in judging whether the defect is a microscopic bubble or a bubble in the drawing process. The first processing unit 41 retrieves these values from the internal memory, obtains the information of the start position ST1 and the detection range E1, and judges the defect type.

In judging the defect type, the first processing unit 41 compares the size of the calculated blob with the minimum blob value, and judges the blob as the defect when the blob area is equal to or larger than the minimum blob value. Then, the size of the defect is compared with the defect type judgment value. When the size of the defect is equal to or smaller than the defect type judgment value, the first processing unit 41 judges the defect as the microscopic bubble. When the size of the defect is larger than the defect type judgment value, the first processing unit 41 judges the defect as the bubble in the drawing process. The position of the detected defect is specified based on the feeding length information of the POF strand 11 obtained by the measurement unit 45. The defect information including the defect type and the position data is stored in the memory 47 by the memory writer 46.

In the explanation above, the operation of the first processing unit 41 is described. The second and third processing units 42, 43 can obtain the defect information in the same manner as explained above. The defect information is stored in the memory 47 together with the identified POF data, and utilized to specify the defect type and the position and remove the defect during the POF winding process and the POF covering process. Then, after the defect is removed, a POF product is manufactured. The defect information is sent to a winding machine and a covering equipment via on-line or a recording medium such as a memory card.

In the above embodiment, the defect is specified based on binary image data, it is possible to other type of image processing to detect the defect. For example, the pixel data (density data) from the line sensor camera may be differentiated to find out extraordinary change in the density data. It is also possible to utilize gray scale to detect the defect in accordance with the change in a density histogram.

Based on the defect position data, it is possible to put a marking on the POF strand 11 to indicate the position of the defect by use of a marking device 50 (see FIG. 1) such as an inkjet printer. In marking the defect posit ion, it is possible to change the color of the marking in accordance with the defect type.

Although the defect portion in the POF strand 11 is removed based on the defect information according to the above embodiment, the defect information may be accumulated to find out if the bubbles are accumulated in a certain part of the POF strand, and may be utilized for searching the reason to generate bubbles in the preform producing process and the drawing process. In that case, an attachment position mark is put in the preform during the preform producing process and the drawing process, and the attachment position mark is set at a predetermined position in each process.

In the above embodiment, the bubbles in the POF strand 11 are detected as the defect, but the present invention is applicable in detecting the defect, such as bubbles and impurities, in other type of the optical fiber (such as the glass optical fiber). Although the line sensor camera 35-37 takes the linear image in the above embodiment, an area image sensor camera may be used to obtain an image of a certain area in the axial direction of the POF strand.

INDUSTRIAL APPLICABILITY

The present invention is applicable in detecting a defect in the optical fiber, such as a plastic optical fiber (POF) and a glass optical fiber.

The invention claimed is:

1. An apparatus for detecting an internal defect in an optical fiber, the apparatus comprising:
   a detection light illumination device for illuminating detection light to the optical fiber from a direction that crosses the axis of the optical fiber;
   an imaging device that takes an image of the optical fiber illuminated by the detection light from a direction that crosses the optical axis of the detection light, and outputs light intensity distribution signals in the radial direction perpendicular to the axis of the optical fiber; and
   a defect detection section that obtains the light intensity distribution signals continuously in the axial direction of the optical fiber, and detects the internal defect based on the level of the light intensity distribution signals in the radial direction and the axial direction,
   wherein the imaging device is a line sensor camera having plural imaging elements in line, and the detection light illumination device is offset from a center axial line of the optical fiber such that the light axis of the illumination is only in the opposite side of the line sensor camera with respect to the center axial line of the optical fiber.

2. The apparatus according to claim 1, wherein more than two pairs of the detection light illumination device and the imaging device are arranged in the axial direction of the optical fiber, and the imaging devices are arranged at a regular interval around the optical fiber.

3. The apparatus according to claim 1, wherein the defect detection section sets a detection start position in which the level of the light intensity distribution signal in the radial direction becomes more than a scan start threshold value, and sets a defect detection range based on the detection start pixel and the type of the optical fiber.

4. The apparatus according to claim 3, wherein the defect detection section sets the detection start position when the line sensor camera repeats to take the image of the optical fiber by a predetermined time.

5. The apparatus according to claim 3, wherein the defect detection section determines the existence of the internal defect based on the size of the portion in the defect detection range in which the level of the light intensity distribution signal is more than a defect judgment value.

6. The apparatus according to claim 5, wherein the defect detection section converts the light intensity distribution signals in the radial and the axial direction into binary data based on the defect judgment threshold value, carries out a blob process to combine the pixels corresponding to the position in which the light intensity signal is more than the second threshold value, and determines the existence of the internal defect when the size of the combined area is a first standard size or more.

7. The apparatus according to claim 6, wherein the defect detection section judges the internal defect as a microscopic bubble when the size of the combined area is a first standard size or more and a second standard size or less, and judges the internal defect as a bubble in a drawing process when the size of the combined area is the second standard size.

8. The apparatus according to claim 1, further comprising a marking device to put a marking on the optical fiber at a position of the defect.

9. The apparatus according to claim 1, wherein the optical fiber has the diameter of 250 µm or more.

10. The apparatus according to claim 1, wherein the optical fiber is a plastic optical fiber strand formed by melt-drawing a preform.

11. An optical fiber manufacturing apparatus having the defect detection apparatus according to claim 1, the optical fiber manufacturing apparatus detecting the internal defect in the optical fiber during the manufacture of the optical fiber.

12. A method for detecting an internal defect in an optical fiber, the method comprising the steps of:
(a) illuminating detection light to the optical fiber from a direction that crosses the axis of the optical fiber;
(b) taking an image, using an imaging device, of the optical fiber illuminated by the detecting light from a direction that crosses the optical axis of the detection light and outputting light intensity distribution signals over the radial direction perpendicular to the axis of the optical fiber;
(c) obtaining the light intensity distribution signals continuously in the axial direction of the optical fiber; and
(d) detecting the internal defect based on the level of the light intensity distribution signals in the radial direction and the axial direction,
wherein the imaging device is a line sensor camera having plural imaging elements in line, and the detection light illumination device is offset from a center axial line of the optical fiber such that the light axis of the illumination light is only in the opposite side of the line sensor camera with respect to the center axial line of the optical fiber.

13. The method according to claim 12, wherein more than two pairs of a detection light illumination device for illuminating the detection light and the imaging device for taking the image of the optical fiber are arranged in the axial direction, and the imaging devices are arranged at a regular interval around the optical fiber.

* * * * *